United States Patent
Burdeinyi et al.

(10) Patent No.: US 12,350,412 B2
(45) Date of Patent: Jul. 8, 2025

(54) DEVICE FOR CREATING A HEALTHY MICROCLIMATE

(71) Applicants: Vasyl Ivanovych Burdeinyi, Pogrebyshhe (UA); Andrii Leonidovych Lapada, Kyiv (UA)

(72) Inventors: Vasyl Ivanovych Burdeinyi, Pogrebyshhe (UA); Andrii Leonidovych Lapada, Kyiv (UA)

( * ) Notice: Subject to any disclaimer, the term of this patent is extended or adjusted under 35 U.S.C. 154(b) by 838 days.

(21) Appl. No.: 17/626,552

(22) PCT Filed: Nov. 20, 2019

(86) PCT No.: PCT/UA2019/000146
§ 371 (c)(1),
(2) Date: Jan. 12, 2022

(87) PCT Pub. No.: WO2021/010929
PCT Pub. Date: Jan. 21, 2021

(65) Prior Publication Data
US 2022/0241453 A1 Aug. 4, 2022

(30) Foreign Application Priority Data
Jul. 18, 2019 (UA) .................................. 2019 08605

(51) Int. Cl.
*A61L 9/22* (2006.01)
*A61G 10/02* (2006.01)
*A61L 9/03* (2006.01)

(52) U.S. Cl.
CPC ................. *A61L 9/22* (2013.01); *A61G 10/02* (2013.01); *A61L 9/032* (2013.01)

(58) Field of Classification Search
None
See application file for complete search history.

(56) References Cited

U.S. PATENT DOCUMENTS 3,505,989 A * 4/1970 Truhan ................. A61G 13/108
 55/467
7,036,502 B2 * 5/2006 Manne ................. A62B 18/003
 128/200.27

(Continued)

FOREIGN PATENT DOCUMENTS

DE 202005008883 3/2006
RU 2223203 2/2004

(Continued)

OTHER PUBLICATIONS

Chagarov et al. RU2433447C1-translated document (Year: 2011).*

(Continued)

*Primary Examiner* — Jelitza M Perez
(74) *Attorney, Agent, or Firm* — Crose Law LLC; Bradley D. Crose

(57) ABSTRACT

The invention relates to apparatuses for air cleaning, sanitation and enrichment, in particular to apparatuses for providing healthful air and generating a healthful micro-climate, and can be used to generate a healthful micro-climate in residential, training, medical treatment and work premises, portable special purpose premises, such as airtight capsules to provide for household, medical and other needs of humans for the air cleaned from harmful impurities, useful in its chemical composition.

The apparatus for providing healthful air and generating the healthful micro-climate configured with a housing, an air intake module with an air intake opening provided on the housing, and a module for supplying cooled or heated and/or humidified air with an air intake opening provided on the housing, comprises a humidification module installed in the housing and connected to a control unit and a module for supplying cooled or heated and/or humidified air and an air (Continued)

temperature sensor connected to the control unit. The housing accommodates at least one container, connected to the control unit, with air useful for health and taken in from the forest area or mountains, or above the sea, or on the sea coast, or cleaned of harmful impurities, or containing added useful admixtures, which is arranged to cool or heat the air from the container, humidify and supply it through the module for supplying cooled or heated and/or humidified air. The apparatus additionally comprises at least two removable air ducts, for connection of which an opening is additionally provided on the housing for each air duct, the each air duct configured to connect to the air intake module and to the module for supplying cooled or heated and/or humidified air, at least one measuring device configured to measure the pressure and/or humidity of the air and/or the amount of harmful impurities therein and/or otherwise and connected to the control unit, the control unit configured, depending on the indicators of at least one measuring device, regulate the power of an air flow supplied through the module for supplying cooled or heated and/or humidified air, through the air intake module and from the container comprising the air, switch the humidification module on and off and activate the air heating and cooling.

The technical result is the expansion of functionality, versatility of use of the apparatus to provide for the use in various conditions and change operating modes of the apparatus, including in emergency situations and hostilities, provide the user with healthful air having the required properties and generate the healthful micro-climate regardless of the type of the premises, its location or the location of the apparatus, climatic conditions of the area and the quality of air in the external environment, provide for the adjustment and use of the apparatus for medical, recreative purposes, at production site, in rescue operations and everyday life, provide for automation of control and regulation of air cleaning, sanitation and enrichment and provide for the safety for the user's health.

13 Claims, 5 Drawing Sheets

(56) References Cited

U.S. PATENT DOCUMENTS

| | | | |
|---|---|---|---|
| 7,296,424 B2 | 11/2007 | Thompson | |
| 2004/0244402 A1* | 12/2004 | Yum | F24F 1/0067 62/411 |

FOREIGN PATENT DOCUMENTS

| | | | | |
|---|---|---|---|---|
| RU | 2223203 C1 * | 2/2004 | | |
| RU | 2414266 | 4/2010 | | |
| RU | 2433447 | 11/2011 | | |
| RU | 2433447 C1 * | 11/2011 | | |
| RU | 122154 | 11/2012 | | |
| RU | 174049 | 9/2016 | | |
| RU | 174049 U1 * | 9/2017 | | F24F 11/00 |
| RU | 178088 | 3/2018 | | |
| RU | 178769 | 4/2018 | | |
| RU | 178769 U1 * | 4/2018 | | |

OTHER PUBLICATIONS

Titkov, V. RU178769U1-translated document (Year: 2018).*
Anna, N. RU174049C1-translated document (Year: 2017).*
Aronin et al. (RU2223203C1)-translated document (Year: 2004).*

* cited by examiner

DEVICE FOR CREATING A HEALTHY MICROCLIMATE

The invention relates to apparatuses for air cleaning, sanitation and enrichment, in particular to apparatuses for providing healthful air and generating a healthful microclimate, and can be used to generate a healthful microclimate in residential, training, medical treatment and work premises, portable special purpose premises, such as airtight capsules to provide for household, medical and other needs of humans for the air cleaned from harmful impurities, useful in its chemical composition.

An apparatus for air treatment is known from the prior art (patent for invention JP 2012181008 A, IPC A61L 9/00, A61L 9/16, F24F 7/00, F24F 7/06, F24F 11/04 published on Sep. 20, 2012), which includes inlet and outlet ducts with respective air openings, an air blower configured to take in contaminated air with an odor that occurs when using an electric heating device, which is not accompanied by combustion, and a control means connected to the air blower, wherein the inlet duct is configured with a deodorizing agent connected to the control means and including the deodorizing agent configured to adsorb, oxidize and decompose air contamination components, and a heating element configured to heat and activate the deodorizing agent, and the air blower is configured to change the intensity of operation as a result of receiving signals from the control means.

The disadvantages of the known analogue are limited functionality and scope of application, the impossibility of adjusting the apparatus in accordance with various operating conditions and using in different conditions, the impossibility of providing the user with healthful air having required properties and generating a healthful micro-climate, the impossibility of providing for automation of control and regulation of air cleaning, which are due to a design solution of the known analogue and the composition of elements thereof.

The known analogue has limited functionality and scope of application, since, as a result of the composition of functional structural elements thereof, it is intended exclusively for cleaning the air from contamination components that are added to the air when using an electric heating device, which is not accompanied by combustion, for example, an electric stove, and elimination of odor of said air components. In spite of the fact that in an embodiment the outlet duct of the known analogue is configured with a cooling device, the known analogue is not able to clean the air of all the contamination components present therein, humidify the air or increase the air temperature etc., which, in turn, does not allow to satisfy the needs of users for provision of healthful air with the required properties and generation of a healthful micro-climate in a premises.

In addition, the known analogue has no ability to exhaust air from a premises or take in air from the external environment, by actually passing through the inlet and outlet ducts the air that is already present in the premises and is subject to re-contamination. The inability to renew the air in a premises, as well as the possibility of the products of oxidation and decomposition of air contamination components and the heated deodorizing agent to enter the air leaving the outlet duct, has a negative effect on the user's health and makes the known analogue hazardous.

In addition, the known analogue is adapted exclusively for connection with a certain type of electrical heating devices, power supply from their power sources and cleaning the air exclusively of the products generated as a result of their operation, which makes it impossible to configure the apparatus in accordance with different operation conditions and use in different conditions. In this case, the control means has no ability to automatically control and regulate the air cleaning, requires manual control with the receipt of signals from the outside about the change in the intensity of the air blower operation, which is inconvenient for the user.

A humidifier for practicing preferably yoga, callanetics or stretching is also known (useful model patent RU 177089 U1, IPC F24F 6/00, F24F 6/12 published on Feb. 7, 2018, Bul. No. 4), which includes a housing on the surface of which the control panel is disposed, the housing accommodates a water reservoir, an ultrasonic transducer that generates vibration in the water of the reservoir and generates a steam flow in the inner chamber that is connected to the atomizer installed at the outlet of the housing, a fan for forced movement of an air flow entering through the air intake opening disposed in the lower part of the housing, a control unit including a printed circuit board with radio elements, a microcontroller, a hygrostat and an information display, which are electrically connected to each other and to the power unit, a light source that executes instructions to generate light at predetermined intervals, temperature and humidity control elements arranged to interact with the inlet air flow, windows for the information display and the control elements that are electrically connected to the printed circuit board are disposed on the control panel, the microcontroller is configured to interact with controls, the information display and the light source; the information display is configured to display predetermined modes of humidification.

The disadvantages of the known analogue are limited functionality and scope of application, the impossibility of adjusting the apparatus in accordance with different operating conditions and using in different conditions, the impossibility of providing the user with healthful air having the required properties and generating a healthful micro-climate, the lack of automation of control and regulation of air humidification, which are due to a constructive solution of the known analogue and the composition of elements thereof.

The known analogue is able to exclusively humidify the air that enters the housing through the air intake opening and exits through the atomizer installed at the outlet of the housing. Thus, the known analogue has no means for cleaning, heating or cooling, aromatizing the air, which makes it impossible to provide the user with healthful air having the required properties and generate a healthful micro-climate because of incomplete treatment and limited influence on the properties of the air in the premises.

In addition, by using the known analogue it is impossible to provide for the removal of contaminated air from the premises and the intake of the air from the external environment, followed by its cleaning, heating or cooling and supply to the premises. Thus, the known analogue distributes in the premises the same volume of non-renewable contaminated and humidified air without the possibility of its renewal, limits the functionality, the scope of application of the known analogue, makes it impossible to use it for various types of premises and in different conditions, provide the user with healthful air having the required properties and generate a healthful micro-climate, and makes the known analogue hazardous to the user's health.

In addition, the known analogue has no means or devices that make it possible to install it outside the premises as configured to supply air to the premises and take in air from the premises, which also limits the functionality of the known analogue and the scope of application thereof. At the same time, the design of the control unit and control panel of the known analogue predetermines the impossibility of automated control and regulation of air humidification by requiring manual control, i.e., interaction with the windows for the information display and control elements, which is inconvenient for the user.

The closest analogue of the invention claimed is a Slogger SL-1103 climatizer (found on May 20, 2019 on the web page on the Internet at https://www.inklimat.ru/catalog/byt-cond/mobilnye/slogger/slogger_sl/) configured to take in air into a premises, heat or cool and/or humidify and ionize and supply it in the premises, wherein the climatizer is configured with a casing configured with wheels, an air intake module with an air intake opening provided on the casing, and a module for supplying cooled or heated and/or humidified and/or ionized air with an opening for air supply provided on the housing, including a humidification module installed in the housing and connected to a control unit and the module for supplying cooled or heated and/or humidified air and an air temperature sensor, air ionizer connected to the control unit, the control unit configured with a control panel disposed on the housing, the air intake opening configured with a dust screen installed on it, the air supply opening configured with horizontal and vertical shutters installed on it, and the humidification module configured with a filter, an air blower direction synchronizer is installed in the housing, connected to the control module and with heat/cold relays installed in parallel and connected to the control module and fan motor.

The disadvantages of the closest analogue are limited functionality, the impossibility of comprehensive use of the apparatus in various conditions and for various purposes, the impossibility of providing the user with healthful air having the required properties with its enrichment and generating a health micro-climate regardless of the type of premises, its location or a location of the apparatus, climatic conditions of the area and air quality in the external environment, complicated control and regulation of cleaning, sanitation and enrichment of air, which are due to the constructive solution of the known analogue and the composition of elements thereof.

Similar to the previous analogues, by using the closest analogue it is impossible to provide for the removal of contaminated air from the premises and the intake of air from the external environment followed by its cleaning, enrichment, heating or cooling and supply to the premises, and it is intended exclusively for installation in the premises for cleaning, humidifying, cooling or heating the constant air contained in said premises, which limits the functionality of the known analogue and the scope of application thereof. Accordingly, the known analogue is configured only with openings for the intake and supply of air and has no means or devices, for example, air ducts providing for the possibility of installing the closest analogue outside the premises at a distance from it, configured to supply air from the external environment to the premises, connect the closest analogue to a breathing mask or other similar devices, it excludes the use thereof in emergency conditions, for medical purposes, in conditions where the premises has a limited volume and the housing cannot be installed in the premises or in a special airtight device.

Since the volume of air contained in a given premises is unchanged and the air is not renewed, the closest analogue cools, humidifies, heats and cleans the air already precooled, humidified, heated, and purified by it, which is ineffective, negatively affects the properties of the air in the premises and health of the user, in particular, in combination with ionization of air, and makes it impossible to provide the user with additional or replaced air, healthful air having the required properties and generate a healthful micro-climate. At the same time, the closest analogue does not provide the possibility of supplying untreated air with predetermined properties to the premises, which also indicates the limited functionality of the closest analogue.

In addition, the design of the control unit of the closest analogue predetermines the impossibility of automated control and regulation of cleaning, sanitation and enrichment of air by requiring manual control, i.e., with the control panel installed in the housing, which is inconvenient for the user and also does not provide for the possibility to use it in various conditions and expand functionality thereof. The constituent elements of the closest analogue do not include measuring devices configured to measure the pressure and/or humidity of the air and/or the amount of harmful impurities therein. In the known closest analogue, only the ability to regulate the generated micro-climate manually and without taking into account the properties of the air in the premises is provided, which makes it impossible to provide the user with healthful air having the required properties and generate a healthful micro-climate regardless of the type of premises, its location or location of the apparatus, climatic conditions of the area and air quality in the environment, use it in emergency and other conditions, as well as for special purposes, for example, for medical, rescue and other purposes.

The technical objective of the invention claimed is to provide a novel apparatus for providing healthful air and generating a healthful micro-climate, which, due to its design features, would be characterized by expanded functionality, comprehensive use, ensuring the possibility to use it in various conditions and with changing operating modes of the apparatus, provide the user with healthful air having the required properties and generate a healthful micro-climate regardless of the type of premises, its location or the location of the apparatus, climatic conditions of the area and air quality in the external environment, ensuring the possibility to adjust and use the apparatus for medical, recreative purposes, at production site, in rescue operations and everyday life, automation configured to automatically adjust a certain type of air, automatically control and regulate cleaning, sanitation and enrichment of the air and safety for the user's health.

The solution to the set technical problem is achieved by the fact that the apparatus for providing healthful air and generating the healthful micro-climate configured with a housing, an air intake module with an air intake opening provided on the housing, and a module for supplying cooled or heated and/or humidified air with an air supply opening provided on the housing, comprises a humidification module installed in the housing and connected to a control unit and the module for supplying cooled or heated and/or humidified air and an air temperature sensor connected to the control unit, according to the disclosure, the housing accommodates at least one container, connected to the control unit, with air useful for health and taken in from the forest area or mountains, or above the sea, or on the sea coast, or cleaned of harmful impurities, or containing added useful admixtures, which is arranged to cool or heat the air from the container, humidify and supply it through the module for supplying cooled or heated and/or humidified air, wherein the apparatus additionally comprises at least two removable air ducts, for connection of which an opening is additionally provided on the housing for each air duct, the each air duct configured to connect to the air intake module and to the module for supplying cooled or heated and/or humidified air, at least one measuring instrument configured to measure the pressure and/or humidity of the air and/or the amount of harmful impurities therein, and/or another, and connected to the control unit, the control unit configured, depending on the indicators of at least one measuring device, to regulate the power of an air flow supplied through the module for supplying cooled or heated and/or humidified air, through the air intake module and from the container comprising the air, switch the humidification module on and off and activate the air heating and cooling.

In this case, according to the disclosure, the apparatus for providing the healthful air and generating the healthful micro-climate is configured with an airtight capsule, in which a housing is installed or connected through at least air ducts, configured to accommodate at least one person therein.

Also, according to the disclosure, the air intake module and the module for supplying cooled or heated and/or humidified air are configured with fans.

At the same time, according to the disclosure, the air intake module is configured with a filter.

In addition, according to the disclosure, the module for supplying cooled or heated and/or humidified air is configured to supply flavoring agents and/or phytoncides and/or medicines and/or otherwise.

At the same time, according to the disclosure, the module for supplying cooled or heated and/or humidified air is configured to connect to a breathing mask or a cap for certain parts of the body (for example, for the treatment of burns by applying special air baths including admixtures of healing and disinfecting substances, etc.).

In addition, according to the disclosure, the housing is configured to be disposed outside the premises, the module for supplying cooled or heated and/or humidified air is connected to one air duct configured to take in the air from the air external environment into the premises, and the air intake module is connected to the other air duct configured to supply the air from the premises.

According to the disclosure, the housing is additionally configured to be installed in the premises, the air intake module is connected to the one air duct configured to exhaust the air into the external environment, and the module for supplying cooled or heated and/or humidified air is connected to the other air duct configured to take in the air from the external environment into the premises.

In addition, according to the disclosure, the temperature sensor and at least one measuring device are disposed outside the housing, and the housing has connectors provided on it for connecting at least one power source and/or the temperature sensor and/or at least one measuring device and/or a display.

At the same time, according to the disclosure, it includes the display configured to visually display indicators of pressure and/or temperature and/or humidity and/or the amount of impurities therein and/or otherwise as measured by the temperature sensor and/or the at least one measuring device.

In addition, according to the disclosure, the control unit is configured with a module for receiving signals from a remote control station or via the Internet.

According to the disclosure, the control unit is additionally connected to a control panel disposed on the housing.

In addition, according to the disclosure, the openings of the air intake module and the module for supplying cooled or heated and/or humidified air are configured to close.

According to the disclosure, the apparatus for providing the healthful air and generating the healthful micro-climate additionally includes an air ionizer installed in the housing and connected to the control module.

According to the disclosure, the apparatus for providing the healthful air and generating the health micro-climate is additionally configured to be powered from a network and/or accumulators and/or solar batteries or other alternative sources.

According to the disclosure, the apparatus for providing the healthful air and generating the healthful micro-climate is additionally configured to be installed in an additional housing and connect to a compressor module for supplying air, or, if necessary, replenish supplies into the air container.

The technical result is the expansion of functionality, the versatility of the use of the apparatus to provide for the use in various conditions and change operating modes of the apparatus, use it not only for domestic purposes, but in a wider range up to emergency medicine, in emergency situations and hostilities, provide the user with healthful air having the required properties and generate the healthful micro-climate regardless of the type of the premises, its location or the location of the apparatus, climatic conditions of the area and quality of air in the external environment, provide for the adjustment and use of the apparatus for medical, recreative purposes, at production site, in rescue operations and everyday life, increase automation with the possibility to automatically adjust to a certain type of air, automation of control and regulation of cleaning, sanitation and enrichment of air, and provide for the safety for the user's health.

The causal relationship between the essential features of the invention and the expected technical result is as follows.

The set of the essential features of the invention claimed provides for said technical result due to the improved design of the housing of the apparatus claimed and the composition of elements of the apparatus claimed, i.e., the presence of at least two removable air ducts, at least one air container, at least one measuring device configured to measure the pressure and/or humidity of the air and/or the amount of harmful impurities therein, and/or otherwise, and as a result of expanding the functionality of the control unit.

An embodiment of the apparatus claimed with at least one container with air, useful for health and taken in from the forest area or the mountains, or above the sea, or on the sea coast, or cleaned of harmful impurities, or containing added useful admixtures, arranged to cool or heat the air from the container, humidify and supply it through the module for supplying cooled or heated and/or humidified air, allows to provide the user with healthful air with the required properties and generate the healthful micro-climate regardless of the type of premises, its location or the location of the apparatus, the climatic conditions of the area and the quality of air in the external environment, since the air from the container can be supplied to the premises with the required settings for the operation of the apparatus claimed in the case where the supply of the air from the external environment is impossible, for example, because of a critical level of the air contamination in emergency situations or ultra-high or ultra-low air temperature, etc. Thus, the user receives the air from the container with the required properties, regardless of any external environment factors or properties of the premises, which is convenient and allows the use of the apparatus claimed for medical and recreative purposes, i.e, for users who need the air with certain properties that cannot be reproduced using other methods, except for the use of a container with air, which has a certain chemical composition, content of useful admixtures, smell, etc.

An embodiment of the apparatus claimed with at least two removable air ducts, for connection of which the housing has additionally provided on it an opening for each air duct, the each air duct configured to connect to the air intake module and to the module for supplying cooled or heated and/or humidified air, makes it possible to connect the removable air ducts to said modules, depending on the properties of air in the external environment and the need for its enrichment and cleaning, the type of premises, the location of the housing, the purposes of using the apparatus claimed, and use the removable air ducts both for supplying air to the premises from the external environment and for exhausting air from the premises, which, in turn, makes it possible to dispose the housing of the apparatus claimed outside the premises, renew the air in the premises with the removal of contaminated air or air with undesirable properties from the premises when disposing the housing of the apparatus claimed in the premises, including airtight one, adjust the apparatus claimed for various modes of operation, depending on the above conditions. Thus, an embodiment of the apparatus claimed with the at least two removable air ducts expands the functionality of the apparatus in comparison with the known analogues, provides for the comprehensive use of the apparatus with the possibility to use it in various conditions and change the operating modes of the apparatus, in emergency situations and hostilities, provides the user with the healthful air having the required properties and with generating the healthful micro-climate regardless of the type of the premises, its location or the location of the apparatus, climatic conditions of the area and quality of air in the external environment, provides for the adjustment and use of the apparatus for medical, recreative purposes, at production site, in rescue operations and everyday life with provision for the safety of the user's health.

An embodiment of the apparatus claimed with the at least one measuring device configured to measure the pressure and/or humidity of the air and/or the amount of harmful impurities therein, and/or otherwise, and connected to the control unit, with the control unit configured, depending on the indicators of the at least one measuring device, to regulate the power of an air flow supplied through the module for supplying cooled or heated and/or humidified air, through the air intake module and from the container containing air, switch the humidification module on and off and activate the heating and cooling of air, allows, if necessary, to fully automate the control and regulation of cleaning, sanitation and enrichment of air, depending on the indicators of the at least one measuring device, without the need for manual control by the user, which is convenient and effective in cases of using the apparatus claimed in the conditions that do not allow the user to adjust the operating modes of the apparatus claimed using manual control, to respond to the indicators of the at least one measuring device, etc.

At the same time, the presence of the at least measuring device in combination with the control unit, which is configured with said capabilities, allows providing the user with the healthful air having the required properties and generating the healthful micro-climate regardless of the type of the premises, its location or the location of the apparatus, climatic conditions of the area and quality of air in the external environment, since the apparatus claimed cleans, cools, heats, humidifies the air, supplies the air to the premises from the container, from the external environment, by responding to the indicators of the at least one measuring device in the current mode and adjusting in accordance with said indicators. Thus, the apparatus claimed generates the micro-climate with the properties required for the user, regardless of the properties of the air in the premises or in the external environment, which also expands the scope of application thereof.

An embodiment of the apparatus claimed with the airtight capsule configured to place at least one person therein, in which the housing is installed or connected to via at least two air ducts, allows using the apparatus claimed when there is a need to completely exclude the access of the air from the external environment without pretreatment thereof, for example, in conditions of emergencies and hostilities, i.e., with significant contamination of air in the external environment, or when there is a need for the sterility of the premises, for example, when performing medical operations in the field conditions.

An embodiment of the air intake module with the filter allows to pre-purify the air that is supplied to the premises before it is cooled and/or humidified and/or heated, which has a positive effect on the properties of the air and allows to provide the user with the healthful air having the required properties, regardless of the climatic conditions of the area and the quality of air in the external environment, which is necessary when using the apparatus claimed, for example, for medical and recreative purposes.

An embodiment of the module for supplying cooled or heated and/or humidified air configured to supply flavoring agents and/or phytoncides and/or medicines and/or otherwise to the air allows to expand the functionality of the apparatus claimed and the scope of application thereof, provide the user with the healthful air having the required properties by imparting the required flavor to the air and cleaning thereof after supplying from the supply module to the module for supplying cooled or heated and/or humidified air.

An embodiment of the module for supplying cooled or heated and/or humidified air configured to connect to the breathing mask allows to use the apparatus claimed for medical purposes, for example, for supplying air with the required properties to a patient with respiratory disease, or for safe breathing in the field conditions, i.e., when a premises is absent, into which the cleaned and enriched air can be supplied, or to the cap for certain parts of the body (for example, for the treatment of burns by applying special air baths including admixtures of healing and disinfecting substances, etc.).

An embodiment of the apparatus claimed with the display configured to visually display the indicators of pressure and/or temperature, and/or humidity and/or the amount of impurities therein, and/or otherwise, measured by a temperature sensor and/or the at least one measuring device, increases the usability of the apparatus claimed, since it allows to provide the user with data on the properties of air in the external environment or in the premises, and on changes in the air properties that occur as a result of the operation of the apparatus claimed.

An embodiment of the temperature sensor and the at least one measuring device disposed outside the housing and an embodiment of the housing with connectors for connecting at least one power source and/or the temperature sensor, and/or the at least one measuring device and/or the display, allows to dispose said devices at a distance from the housing of the apparatus claimed, expands the scope of application of the apparatus claimed and allows disposing the housing outside the premises without losing the functionality by the apparatus claimed.

An embodiment of the control unit with the module for receiving signals from the remote control station, via the Internet or as connected to the control panel disposed on the housing, increases the usability of the apparatus claimed and provides for the versatility of the use thereof in various conditions, including when there is a need to configure the operating mode of the apparatus claimed manually using signals from the remote control station, via the Internet or from the control panel disposed on the housing.

An embodiment the openings of the air intake module and the module for supplying cooled or heated and/or humidified air configured to close allows, if necessary, to close these openings using dampers, valves or other similar means and thereby urgently terminate the operation of the apparatus claimed, as well as provides comprehensive use the apparatus claimed, since it allows, for example, to exclusively take in the air from the premises or exclusively supply the air to the premises.

An embodiment of the apparatus claimed with the air ionizer installed in the housing and connected to the control module allows to effectively clean the air supplied to the module for supplying cooled or heated and/or humidified air of harmful substances and pathogens.

The design of the apparatus claimed for providing the healthful air and generating the healthful micro-climate is explained using the following drawings:

Figure 1:
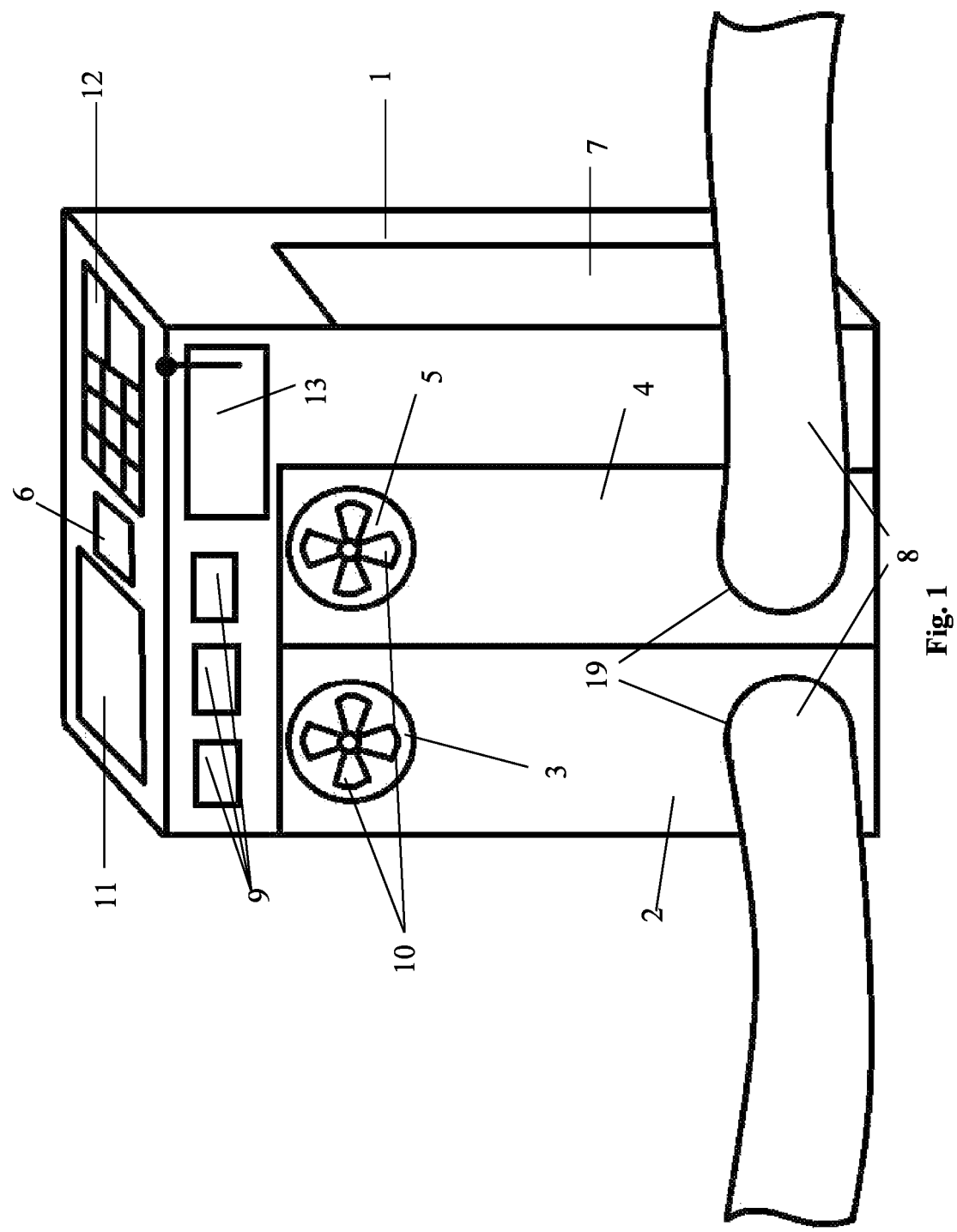
FIG. 1 is a general view of the apparatus claimed for providing the healthful air and generating the healthful micro-climate according to an embodiment.
Figure 2:
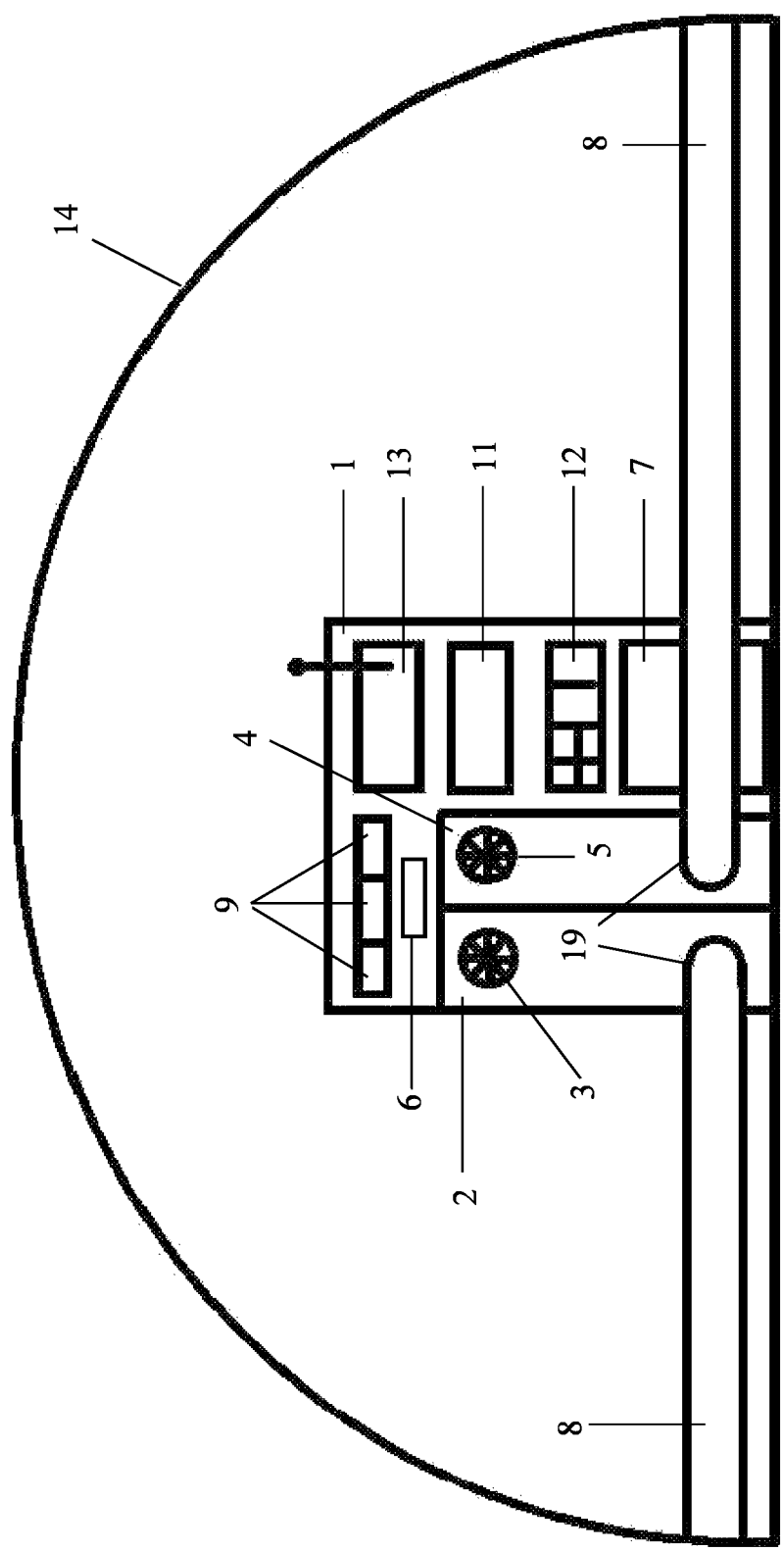
FIG. 2 shows the apparatus claimed for providing the healthful air and generating the healthful micro-climate, the housing of which is installed in the airtight capsule, according to an embodiment.
Figure 3:
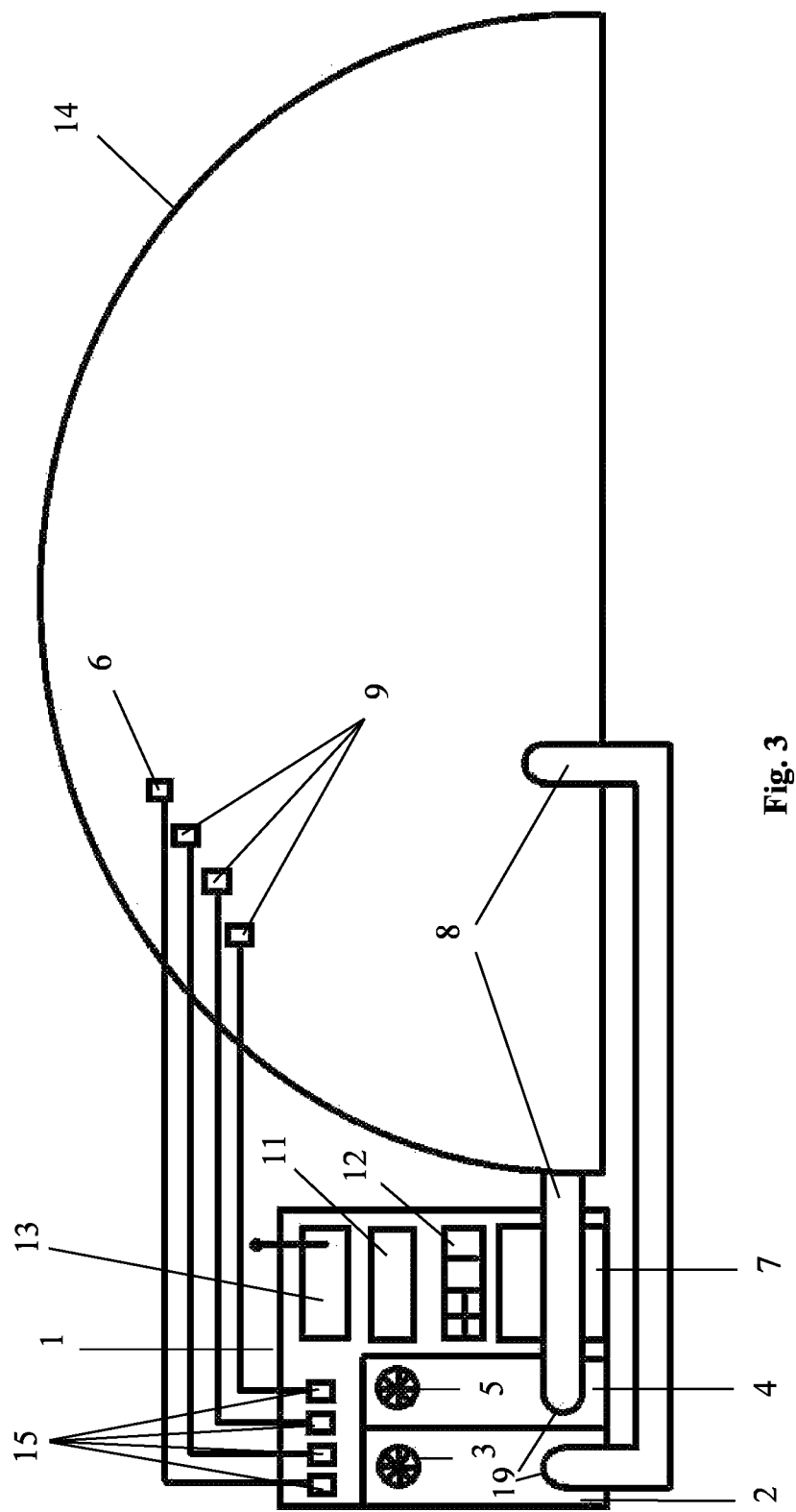
FIG. 3 shows the apparatus claimed for providing the healthful air and generating the healthful micro-climate, the housing of which is disposed outside the premises or the capsule, according to an embodiment.
Figure 4:
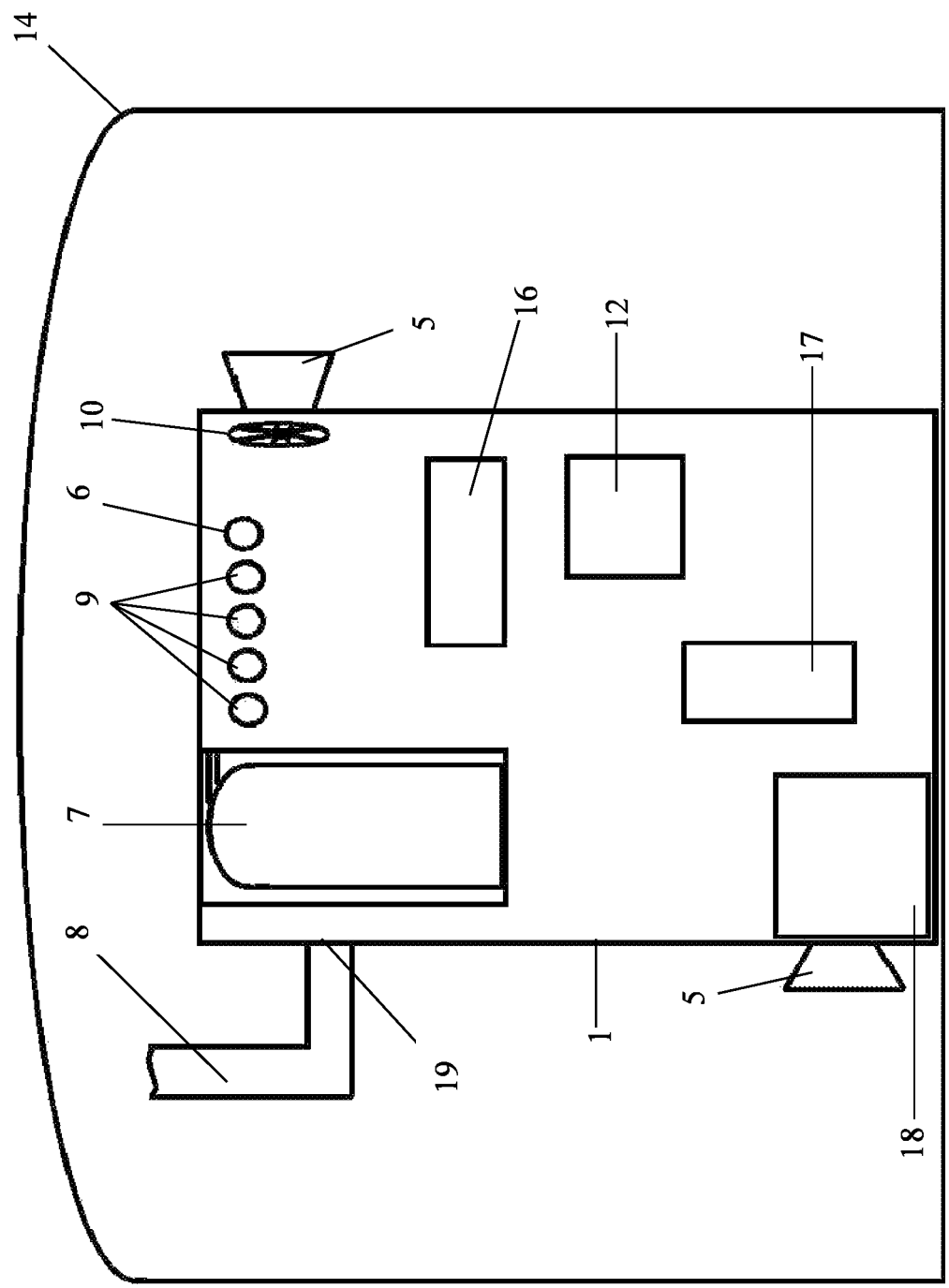
FIG. 4 is a schematic illustration of the constituent elements of the apparatus claimed for providing the healthful air and generating the healthful micro-climate according to an embodiment.
Figure 5:
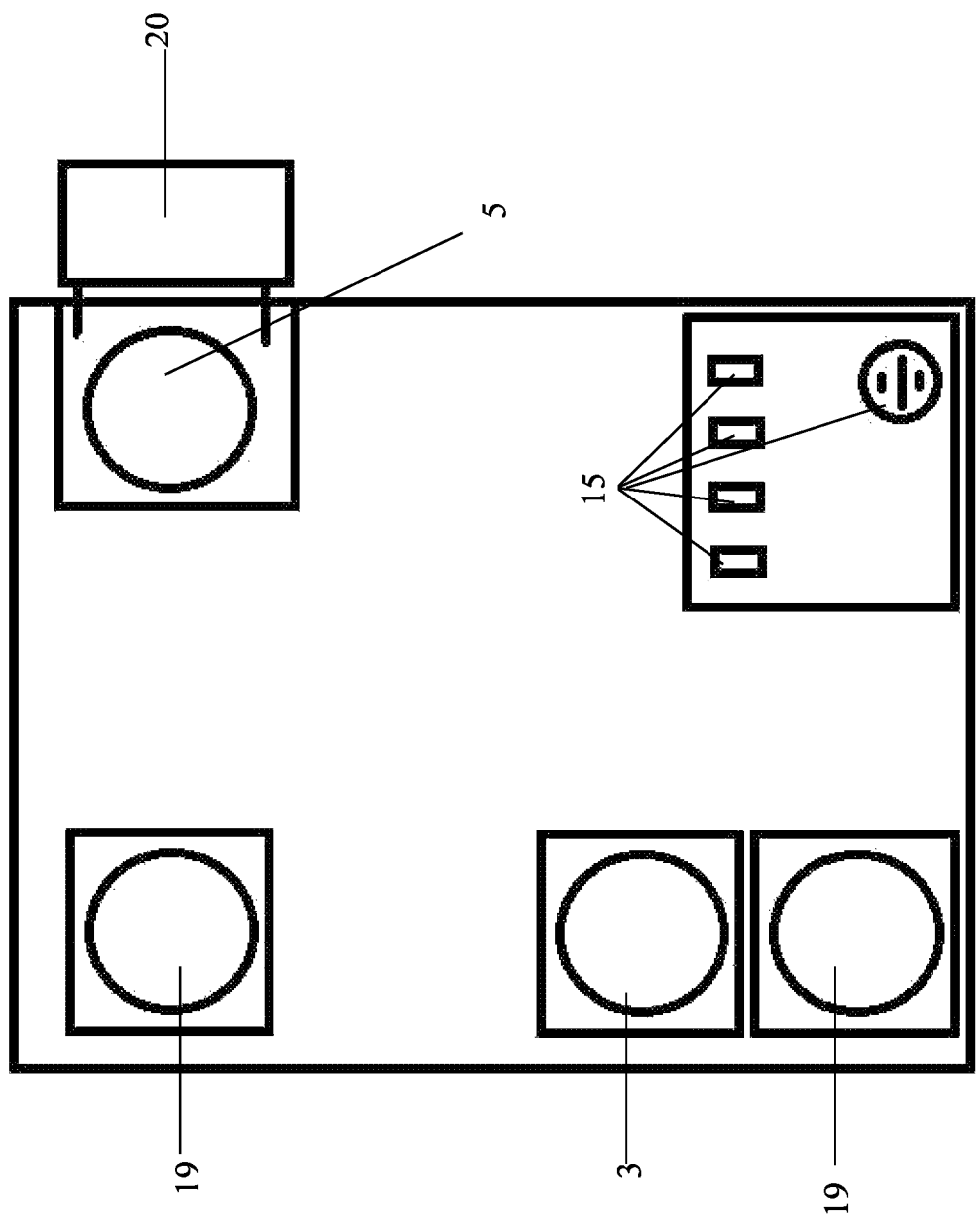
FIG. 5 is a schematic illustration of the openings and connectors of the apparatus claimed for providing the healthful air and generating the healthful micro-climate according to an embodiment.

The drawings schematically show preferred, but not exclusive, embodiments of the apparatus claimed for providing the healthful air and generating the healthful micro-climate, configured with a housing 1, an air intake module 2 with an air intake opening 3 provided on the housing, a module for supplying cooled or heated and/or humidified air 4 with an air supply opening 5 provided on the housing, a control unit 16, a humidification module 18, an air temperature sensor 6, an air container 7, two removable air ducts 8, and measuring devices 9.

In addition, in an embodiment, the apparatus claimed is configured with a heating element 17, a display 11, and the control unit is connected to a control panel 12 disposed on the housing 1, and is configured with a module for receiving signals 13 from a remote control station, and the removable air ducts 8 are connected to openings 19 for the air ducts.

The housing 1 is a receptacle for the main constituent elements of the apparatus claimed, additionally configured with the openings 19 for connecting each air duct. In an embodiment, the apparatus claimed is configured with an airtight capsule 14, in which the housing 1 is installed or connected to through at least the air ducts 8. The housing 1 can be disposed in the airtight capsule 14 configured to accommodate at least one person in or outside it. The airtight capsule 14 may additionally be part of the housing 1 configured with the receptacle, for example, such as a compartment or container for accommodating the airtight capsule 14 configured to be installed in said receptacle. When working in hangars, premises having a large area, etc., where the surrounding gas environment is present not comfortable or harmful to humans, the apparatus can be disposed in the airtight capsule 14 of various sizes arranged for 1 to several persons to stay or work therein. The housing 1 may additionally be disposed in the airtight capsule 14 when disposing the apparatus claimed in an open area, for example, during a sandstorm or when working in a contaminated or infected zone.

The housing 1 may additionally be installed in any premises or disposed outside a premises, and can also be made of materials with increased strength and with wheels or other means for transporting thereof. Additionally, in an embodiment, the housing accommodates the control unit 16, the heating element 17 and the humidification module 18, wherein the housing may include devices or means for cleaning, cooling and aromatizing air.

The air intake module 2 is disposed in the housing 1 and is configured with the air intake opening 3, in which a fan 10 is installed. At the same time, the air intake from the environment or from the premises may be carried out using pumps or other devices that are part of the air intake module 2 or disposed directly within the air intake opening 3. In a preferred embodiment, the air intake module 2 is provided with at least one filter. In addition, in a preferred embodiment, the air intake opening 3 is configured to close.

The module for supplying cooled or heated and/or humidified air 4 is disposed in the housing 1, connected to the humidification module 18 and is configured with the air supply opening 5, in which the fan 10 is installed. However, the air supply from the module for supplying cooled or heated and/or humidified air 4 may be provided with other devices, for example, a compressor, which, if necessary, can replenish the air supplies in the container 7. In addition, the apparatus for providing the healthful air and generating the healthful micro-climate can be configured to be installed in an additional housing and to connect to a compressor module for air supply, or, if necessary, replenish supplies in the air container 7.

In an embodiment, the air intake opening 3 and/or the air supply opening 5 can be configured to close the lattice cover 20.

In addition, the module for supplying cooled or heated and/or humidified air 4 can be connected to the heating element 17, devices or means for air cooling, air cleaning, for example, an ionizer disposed in the housing 1, and can be configured to supply flavoring agents and/or phytoncides and/or medicines, and/or otherwise to the air, configured to connect to a breathing mask, cap, or other similar devices. In a preferred embodiment, the air supply opening 5 is configured to close.

The air temperature sensor 6 is designed to measure the air temperature in the premises or in the external environment, is connected to the control unit and can be disposed both in the housing 1 and outside the housing 1 with connecting to the housing 1 via the connector 15.

The container 7 with air useful for health and taken in form the forest area or the mountains, or above the sea, or on the sea coast, or cleaned of harmful impurities, or containing added useful admixtures, is arranged to cool or heat the air from the container 7, humidify and supply it through the module for supplying cooled or heated and/or humidified air 4. This air container 7 may include a bladder, container, tank or other vessel for said air and may be connected to the heating element 17, the devices or means for air cooling, air cleaning, for example, the ionizer disposed in the housing 1.

The two removable air ducts 8 are configured to connect to the air intake module 2 and to the module for supplying cooled or heated and/or humidified air 4. In a depicted embodiment, the removable air ducts 8 are pipes of flexible material, each connected to a respective opening for the air duct 19.

In a depicted embodiment of the apparatus claimed, the measuring devices 9 are configured to measure atmospheric pressure, air humidity and the amount of harmful impurities therein and are connected to the control unit 16. The measuring devices 9 may be disposed in the housing 1 or may be connected thereto via the connectors 15.

The display 11 is configured to visually display indicators of air pressure and/or temperature and/or humidity and/or the amount of impurities therein and/or otherwise as measured with the temperature sensor 6 and/or the at least one measuring device 9. The display 11 may be disposed in the housing 1 or may be connected thereto via the connector 15.

The control panel 12 is disposed on the housing 1, is connected to the control unit 16 and intended for manual control of the operation of the apparatus claimed, for example, by pressing buttons or using a touchscreen system or through the user's interaction with other control means.

The module for receiving signals 13 from the remote control station is disposed on the housing 1, is connected to the control unit 16 and intended for manual control of the operation of the apparatus claimed by sending signals from the remote control station.

In an embodiment, the apparatus claimed may be connected via the connectors 15 to an electrical network and/or accumulators and/or solar batteries or other alternative power sources.

The control unit 16 is configured, depending on the indicators of the at least one measuring device 9, to regulate the power of an air flow supplied through the module for supplying cooling or heated and/or humidified air 4, through the air intake module 2 and from the container 7 which contains air, turn on and off the humidification module 18 and activate the heating element 17, the devices or means for cleaning and cooling the air disposed in the housing 1. The control unit 16 can be a controller or other similar device.

The humidification module 18 is connected to the control unit 16 and the module for supplying cooling or heated and/or humidified air 4 and is installed in the housing 1. In a preferred embodiment, the humidification module 18 is configured with a container for water, which can be in the container in a liquid or frozen state and is configured to be replenished without interrupting the operation of the apparatus claimed.

The apparatus claimed for providing the healthful air and generating the healthful micro-climate is used as follows.

Initially, the mode of operation of the apparatus claimed is selected, depending on the user's needs, current conditions, type of the premises and planned purposes of use etc., and the housing 1 of the apparatus claimed is installed in the premises or outside it.

If a need arises to treat a small amount of air in the premises and slightly change in its properties, the housing 1 is installed in the premises, and the removable air ducts 8 are not connected to the openings for the air ducts 19, by closing these openings, for example, with covers or dampers. In this mode, the air intake module 2 takes in air from the premises with the subsequent supply of the air to the humidification module 18, to the heating element 17, to the devices or means for cleaning and cooling air disposed in the housing 1, following which the air enters the module for supplying cooled or heated and/or humidified air 4 and is supplied to the premises through the air supply opening 5. In this case, the control unit 16 or the user, using the control panel 12 or the remote control station and the module for receiving signals 13, can set the air supply from the air container 7 to the module for supplying cooled or heated and/or humidified air 4 with cooling or heating the air from the container 7 and/or humidifying thereof, if necessary.

In said mode, if there is a need for supplying air from the external environment or taking in air from the premises, one of the removable air ducts 8 is connected to one of the openings for the air ducts 19.

If there is a need for cleaning, enrichment, renewal of air in the premises which is isolated from the external environment, the housing 1 is installed in the premises, the air intake module 2 is connected to one of the air duct 8 configured to exhaust air to the external environment, and the module for supplying cooled or heated and/or humidified air 4 is connected to the other air duct 8 configured to take in air of the external environment into the premises. In this mode, the air intake module 2 takes in contaminated air from the premises, which is discharged into the external environment through the one removable air duct 8, and the other removable air duct 8 takes in air from the external environment with the subsequent supply of the air to the humidification module 18, to the heating element 17, to the devices or means for cleaning and cooling air disposed in the housing 1, following which the air enters the module for supplying cooled or heated and/or humidified air 4 and is supplied to the premises through the air supply opening 5. In this case, the control unit 16 or the user, using the control panel 12 or the remote control station and the module for receiving signals 13, can set the air supply from the air container 7 to the module for supplying cooled or heated and/or humidified air 4 with cooling or heating the air from the container 7 and/or humidifying thereof, if necessary.

If there is a need for cleaning, enrichment, renewal of air in a premises that is isolated from the external environment without installing the housing 1 in this premises, the housing 1 is disposed outside the premises, the module for supplying cooled or heated and/or humidified air 4 is connected to the one air duct 8 configured to take in air from the air external environment into the premises, and the air intake module 2 is connected to the other air duct 8 configured to supply the air from the premises. The temperature sensor 6 and the measuring devices 9 are installed in the premises by connecting them to the control unit 16 via the connectors 15. In this mode, the air intake module 2 takes in air from the external environment through the air intake opening 3, with the subsequent air supply to the humidification module 18, the heating element 17, the devices or means for cleaning and cooling air disposed in the housing 1, following which the air enters the module for supplying cooled or heated and/or humidified air 4 and is supplied to the premises through the one removable air duct 8. The other air duct 8 takes in the contaminated air from the premises with the subsequent exhausting of the air through the module for supplying cooled or heated and/or humidified air 4 to the external environment. In this case, the control unit 16 or the user, using the control panel 12 or the remote control station and the module for receiving signals 13, can set the air supply from the air container 7 to the module for supplying cooled or heated and/or humidified air 4 with cooling or heating the air from the container 7 and/or humidifying thereof, if necessary.

Thus, the apparatus claimed for providing the healthful air and generating the healthful micro-climate can be comprehensively used in several different modes depending on the user's needs, type of the premises, the intended purposes of use and other factors with the replacement, full or partial, of air in the premises or capsule, which makes the scope of application thereof much wider than that of the known analogues and makes the apparatus claimed universal for any existing conditions. In this case, the operation of the apparatus claimed can be fully automated without manual control by the user.

The existing sources of patent and scientific and technical information do not reveal an apparatus for providing healthful air and generating a healthful micro-climate, which has the claimed set of essential features, therefore, the presented technical solution meets the "novelty" criterion.

A comparative analysis of said technical solution with the closest analogue has showed that the implementation of the set of essential features characterizing the provided invention results in the emergence of said qualitatively new technical properties, the set of which has been previously established from the state of the art, which allows to conclude that the provided technical solution meets the "inventive step" criterion.

The provided technical solution is industrially applicable, since it does not include any structural elements and materials that cannot be reproduced at the present stage of development of technology in the conditions of industrial production.

What is claimed is:

1. An apparatus for providing healthful air and generating a healthful micro-climate configured with a housing, an air intake module with an air intake opening provided on the housing, and a module for supplying cooled or heated and/or humidified air with an air supply opening provided on the housing, comprising a humidification module installed in the housing and connected to a control unit and the module for supplying cooled or heated and/or humidified air, and an air temperature sensor connected to the control unit, wherein the housing accommodates at least one container, connected to the control unit, with air useful for health and taken in from the forest area or mountains, or above the sea, or on the sea coast, or cleaned of harmful impurities, or containing added useful admixtures, wherein the humidification module is arranged to cool or heat the air from the container, humidify and supply it through the module for supplying cooled or heated and/or humidified air, wherein the apparatus additionally comprises at least two removable air ducts, for connection of which an opening is additionally provided on the housing for each air duct, each air duct configured to connect to the air intake module and to the module for supplying cooled or heated and/or humidified air, at least one measuring device configured to measure the pressure and/or humidity of the air and/or the amount of harmful impurities therein, and/or another, and connected to the control unit, the control unit configured, depending on the indicators of at least one measuring device, to regulate the power of an air flow supplied through the module for supplying cooled or heated and/or humidified air, through the air intake module and from the container comprising the air, switch the humidification module on and off and activate the air heating and cooling, wherein the apparatus is configured to be installed in an additional housing and connect to a compressor module for supplying air, or, if necessary, replenish supplies into the air container.

2. The apparatus for providing the healthful air and generating the healthful micro-climate according to claim 1, wherein it is configured with an airtight capsule, in which the housing is installed or connected through the at least two removable air ducts, configured to accommodate at least one person therein.

3. The apparatus for providing the healthful air and generating the healthful micro-climate according to claim 1, wherein the air intake module and the module for supplying cooled or heated and/or humidified air are configured with fans.

4. The apparatus for providing the healthful air and generating the healthful micro-climate according to claim 1, wherein the air intake module is configured with a filter.

5. The apparatus for providing the healthful air and generating the healthful micro-climate according to claim 1, wherein the module for supplying cooled or heated and/or humidified air is configured to supply flavoring agents and/or phytoncides and/or medicines and/or otherwise.

6. The apparatus for providing the healthful air and generating the healthful micro-climate according to claim 1, wherein the module for supplying cooled or heated and/or humidified air is configured to connect to a breathing mask or a cap.

7. The apparatus for providing the healthful air and generating the healthful micro-climate according to claim 1, wherein the module for supplying cooled or heated and/or humidified air is connected to one of the at least two removably air ducts configured to take air from the air external environment into the premises, and the air intake module is connected to another of the at least two removable air ducts configured to supply the air from the premises.

8. The apparatus for providing the healthful air and generating the healthful micro-climate according to claim 1, wherein the air intake module is connected to one of the at least two removably air ducts configured to exhaust the air into the air external environment into, and the module for supplying cooled or heater and/or humidified air is connected to another of the at least two removable air ducts configured to take in the air from the external environment into the premises.

9. The apparatus for providing the healthful air and generating the healthful micro-climate according to claim 1, wherein the air temperature sensor and at least one measuring device are disposed outside of the housing and the housing has connectors provided on it for connecting at least one power source and/or the air temperature sensor and/or at least one measuring device and/or display.

10. The apparatus for providing the healthful air and generating the healthful micro-climate according to claim 1, wherein the control unit is configured with a module for receiving signals from a remote control station or via the Internet.

11. The apparatus for providing the healthful air and generating the healthful micro-climate according to claim 1, wherein openings of the air intake module and the module for supplying cooled or heated and/or humidified air are configured to close.

12. The apparatus for providing the healthful air and generating the healthful micro-climate according to claim 1, wherein it comprises an air ionizer installed in the housing and connected to the control unit.

13. The apparatus for providing the healthful air and generating the healthful micro-climate according to claim 1, wherein it is configured to be powered from a network and/or accumulators and/or solar batteries or other alternative sources.

* * * * *